United States Patent [19]
Weichselbaum

[11] 4,116,338
[45] Sep. 26, 1978

[54] PACKAGE FOR STERILE ARTICLE

[75] Inventor: Edwin Gordon Weichselbaum, Eureka, Mo.

[73] Assignee: Sherwood Medical Industries Inc., St. Louis, Mo.

[21] Appl. No.: 838,422

[22] Filed: Sep. 30, 1977

[51] Int. Cl.² ............................................. B65D 19/02
[52] U.S. Cl. .................................. 206/610; 206/63.3; 206/363; 229/56
[58] Field of Search ................... 229/56; 206/0.5, 363, 206/364, 63.3, 438, 439, 306, 440, 441, 484, 610, 611, 634, 820

[56] References Cited

U.S. PATENT DOCUMENTS

| | | | |
|---|---|---|---|
| 2,845,173 | 7/1958 | Langdon | 206/363 |
| 3,126,629 | 3/1964 | Claisse et al. | 206/484 |
| 3,315,802 | 4/1967 | Lonholdt et al. | 206/63.3 |
| 3,768,725 | 10/1973 | Pilaro | 206/439 |
| 3,809,228 | 5/1974 | Fowler et al. | 206/306 |
| 3,941,245 | 3/1976 | Oliverius | 206/438 |
| 4,026,751 | 5/1977 | Fowler et al. | 206/306 |

FOREIGN PATENT DOCUMENTS 1,251,466  12/1961  Fed. Rep. of Germany .......... 206/63.3

*Primary Examiner*—William Price
*Assistant Examiner*—Bruce H. Bernstein
*Attorney, Agent, or Firm*—Stanley N. Garber; William R. O'Meara

[57] ABSTRACT

A package for a sterile article has a pair of sterile panels, a sterile article between the panels, and a bacteria-impervious envelope enclosing the panels and the article. The envelope has a tear-line for manually separating it into two open-ended portions for the purpose of opening the envelope. The panels extend outwardly beyond the tear-line so that after the envelope is opened, the panels and the article remain within one of the envelope portions with the panels extending out of that envelope portion. In this way, the article can be removed from the panels and envelope portion without the article contacting any part of the envelope portion.

17 Claims, 4 Drawing Figures

PACKAGE FOR STERILE ARTICLE

BACKGROUND OF THE INVENTION

This invention relates to packages for sterile articles and more particularly to a package of this type which avoids contamination of the article when it is removed from the package.

One of the problems with some prior art packages for sterile articles is that the removal of the article from the package causes it to become contaminated. For example, in the case of surgical devices, it is often desirable to open the package and drop the device out of the open end of the package onto a sterile field. Unless great care is taken, the device may contact the package at the edge of the opening, which edge can be contaminated by the exterior surface of the package resulting in contamination of the device.

In U.S. Pat. No. 2,845,173, a package is disclosed which allows an article to be removed from the package without contacting the edge of the opening. However, this package has a body section and an end closure section that must be severed transversely across an end and longitudinally along opposed sides of the closure section. Then, the parts of the closure section are peeled back to expose the opening in the body section through which the article is removed. Thus, this package has the disadvantage that it requires a rather complicated opening procedure.

In U.S. Pat. No. 2,902,146, a sack containing the article is disposed within a casing. The casing is transversely severed, the sack removed from the casing, and the article then removed from the sack. A disadvantage of such a package lies in the fact that it requires removal of an internal sack from a portion of the casing and then removal of the article from the sack, thus providing a rather complicated removal procedure.

In U.S. Pat. No. 3,112,031, an article is disposed in a wrapper having a separate closure cap, with a wrapper and the cap disposed within an envelope. An end portion of the envelope is severed to provide an opening and the package is manipulated to push the closure cap and an end portion of the wrapper through the opening in the envelope. The cap falls off the wrapper after the open end of the wrapper is beyond the open end of the envelope. The wrapper is then deformed into substantially tubular form so that the article may slide out of the wrapper. This package has the disadvantage of requiring a cap which adds to the number of parts and increases the cost of assembling the package. The removal procedure is complicated by the fact that the end portion of the envelope is removed, an inner container then moved relative to the envelope to drop the cap, and then the article must be removed from the inner container.

SUMMARY OF THE INVENTION

Accordingly, it is an object of the present invention to provide an improved package for a sterile article which is simple and economical in construction, which allows the packaged article to be removed from the package without being contaminated, allows the article to be removed in a simple and quick manner, and, in general, avoids the above-mentioned disadvantages of the prior art packages.

In accordance with one form of the present invention, a package is provided which includes a pair of sterile panels of sheet material, a sterile article between the panels, and an envelope sealingly enclosing the panels. The envelope is provided with a tear-line of weakness for opening the envelope and the panels extend across the tear-line so that after the envelope is opened, the article can be moved outwardly from between the panels without contacting any portion of the envelope.

These as well as other objects and advantages of the present invention will become apparent from the following detailed description and accompanying drawing.

DESCRIPTION OF THE PREFERRED EMBODIMENT

Figure 1:
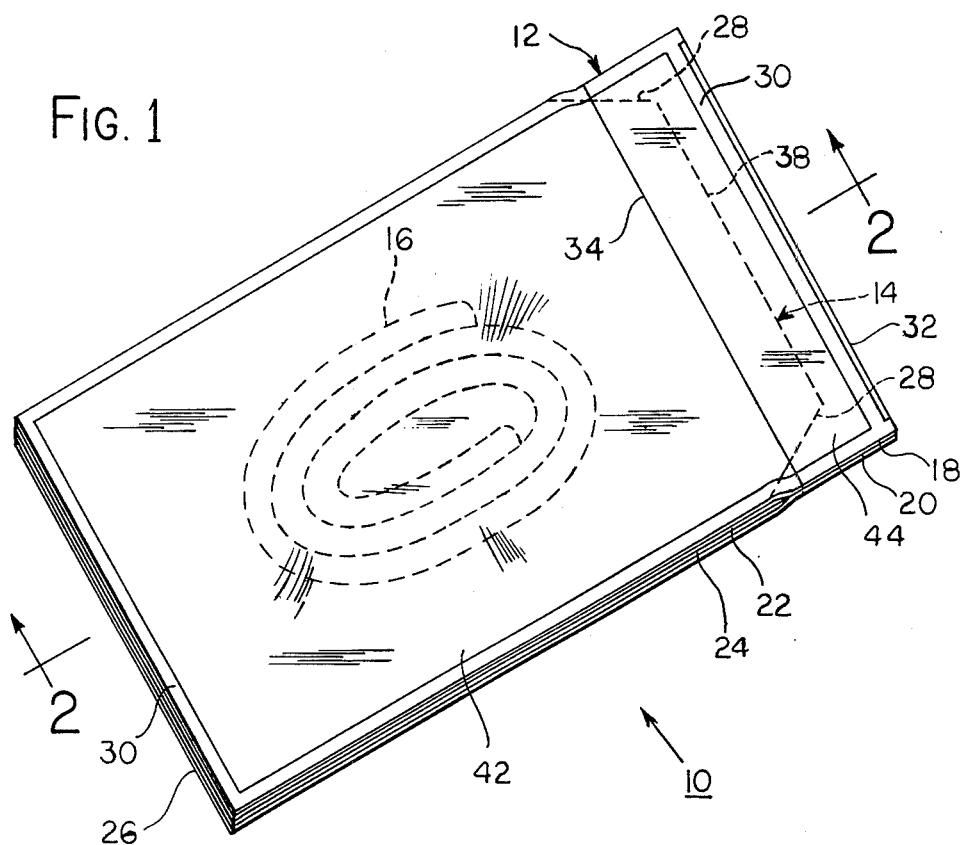
FIG. 1 is a perspective view of a package in accordance with a preferred embodiment of the present invention.
Figure 2:
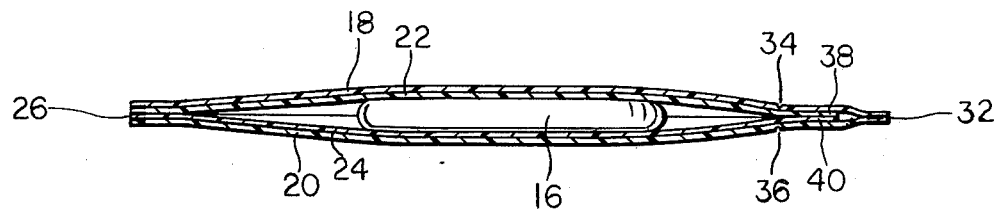
FIG. 2 is a cross-sectional view taken along line 2—2 of FIG. 1.

Referring now to the drawing, and particularly to FIGS. 1 and 2, a deformable package 10 is shown including an outer envelope 12 sealingly enclosing an inner pouch 14 which contains a sterile article 16. Article 16 is shown in the illustrated embodiment as a medical or surgical tube or catheter.

Figure 3:
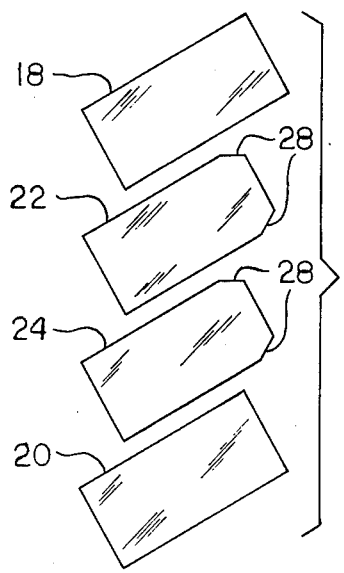
FIG. 3 is a perspective view on a reduced scale illustrating the panels employed in the package of FIG. 1 but before they are assembled.

The envelope 12 is formed of a pair of facing panels 18 and 20, and the pouch 14 is formed of a pair of facing panels 22 and 24, these panels being shown also in FIG. 3. These four panels are preferably formed of a suitable flexible thermoplastic material which is bacteria-impervious but preferably pervious to a sterilizing gas, such as ethylene oxide, so that the completed package, including the article, can be sterilized. The panels may, for example, be formed of polyethylene or of other plastic sheet material, or a suitable paper, such as glassine paper, may be used.

The four thermoplastic panels 18, 20, 22 and 24 are shown in FIGS. 1 and 2 in aligned stacked relation with the article 16 disposed between the inner two panels 22 and 24. The end edges of the panels are coplanar at the lower end 26 of the package. The inner panels are of shorter length than the outer panels and each is provided with a pair of upper, inwardly angled edges 28. As seen in FIG. 1, the four plastic panels are welded together along a marginal or peripheral weld, indicated at 30, which extends entirely around the stacked panels. The inner panels of the pouch are welded transversely along the bottom ends and longitudinally along the opposed sides between the bottom ends and the angled edges 28 but the pouch is open at its upper end. The outer panels are welded entirely around the periphery with the areas above the inner panels at the upper end 32 of the package, welded together in direct face-to-face contact. The weld 30 completely seals the package against the ingress of bacteria and other foreign matter and is formed by any suitable or conventional plastic welding apparatus. In some cases, depending upon the materials used in making the envelope 12 and pouch 14, a suitable cement may be employed to connect the panels together instead of welding them together.

The envelope 12 is provided with tear-lines of weakness 34 and 36 formed in the outer sides of the outer layers 18 and 20 respectively. These tear-lines are in the form of parallel grooves extending transversely between the opposed sides of the envelope near, but spaced from, the upper end 32 of the envelope. The tear-lines together form a substantially continuous tear-line of weakness extending entirely around the envelope. The inner layers 22 and 24 extend across tear-lines 34 and 36 and terminate longitudinally between the tear-lines and the upper end of the envelope. The tear-lines may be formed by suitable or conventional heating elements used for this purpose.

Since all four layers are heat-sealed or welded together in facing relation along marginal portions of the opposed sides of the illustrated envelope, the tear-lines 34 and 36 are located close enough to the upper end 32 of the envelope such that they cross the weld 30 at places where only the outer layers 18 and 20 are welded together in direct contact facing relation. As seen in FIG. 1, the tear-lines cross the angled edges 28 of the inner layers 22 and 24. The angled edges 28 of the inner layers form flaps 38 and 40 of slightly less width then the envelope and are not welded to the envelope. The inner layers 22 and 24 of the pouch extend across the tear-lines with the flaps 38 and 40 being at the open end of the pouch.

Figure 4:
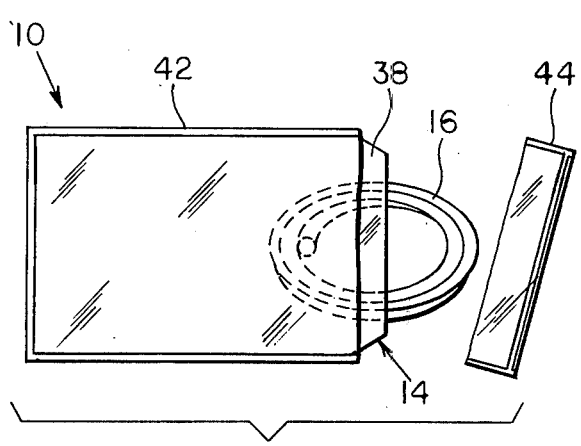
FIG. 4 is a plan view, on a reduced scale, illustrating the package of FIG. 1 after it has been opened.

With this construction, the tear-lines 34 and 36 divide the envelope 12 into separable portions 42 and 44, these portions separating on the tear-lines to open the package 10 when manually grasped and urged in opposite directions. Once the tear-lines 34 and 36 are broken, the envelope portion 44 is free to move from the rest of the package. FIG. 4 shows the package 10 opened with the envelope portions 42 and 44 separated. Portion 42, in the illustrated embodiment, is connected by weld 30 to the two inner layers 22 and 24 so that the pouch 14 remains with portion 42.

After the right-hand portion 44 is removed to open the package 10, the portion 42 containing the inner layers and article 16 may be turned so that the article 16 drops out from the inner layers and portion 42 onto a sterile field. Since the upper end portions or flaps 38 and 40, respectively, of the inner layers 22 and 24 extend beyond the upper end edges of the envelope portion 42, which end edges are produced by the broken tear-lines, the article 16 moves along the inner surfaces of the sterile inner layers and through the open end of portion 42 without contacting the open end edge of portion 42. Thus, the article 16 is removed from the package 10 without being contaminated by the edge about the opening of the envelope 12.

Where desired, instead of employing the inner layers 22 and 24 of sheet material and welding them between the outer layers of the envelope 12 to form a sterile chamber as shown, a separate sack or bag could be formed, for example, by forming a seamless plastic tube, such as an extruded tube, and flattening it. Such a tube could be inserted along with the article between the outer layers of the outer envelope and only the outer layers of the envelope welded together. The outer envelope could also be formed in many other ways, for example, one way is to cut it from an extruded tube and subsequently seal the opposed ends after it receives the inner pouch with the article in it.

If desired, one or both flaps 38 and 40 of the inner layers may be folded inwardly and toward the lower end 29 of the package and be disposed within the envelope portion 42. In such case, after the package is opened, the inwardly folded-back flap or flaps could be engaged and moved outwardly of the envelope portion 42 by the article as it moves out of the package. Since the flaps would extend beyond the end of the open envelope portion 42, they would prevent contact between the article and that envelope portion.

It will now be apparent that there has been provided a package for a sterile article which is economical to make, quickly and easily opened, and which substantially obviates contamination of the article upon removal from the package.

As various changes could be made in the above disclosure without departing from the scope of the invention, it is intended that all matter in the above description and shown in the accompanying drawing shall be interpreted as illustrative and not in a limiting sense.

What is claimed is:

1. A sterile package comprising a pair of sterile panels of sheet material in facing relation, a sterile article disposed between said panels, and an envelope sealingly enclosing said panels and article, said envelope having a weakened area for manually tearing said envelope to provide an opening in said envelope, said panels having a portion thereof immovably restrained relative to said envelope before and after said envelope is opened, said panels extending longitudinally across the edge of said opening in said envelope after it is opened so that when said article is removed from between said panels it will not contact said envelope.

2. The package of claim 1 wherein said weakened area divides said envelope longitudinally into a pair of separable envelope portions that are open-ended when pulled apart to open said envelope, said panels remain with one of said envelope portions after said envelope is opened and extend externally of said one envelope portion.

3. The package of claim 2 wherein said panels are fixedly connected to said one envelope portion.

4. The package of claim 2 wherein said panels form a pouch within said envelope enclosing said article and having at least one open end for movement of the article therethrough after the package is opened.

5. The package of claim 4 wherein said envelope comprises a pair of panels of sheet material, and wherein said pouch panels are disposed between said envelope panels, said envelope panels being sealed together entirely around said envelope, and said pouch panels being sealed together and to said envelope panels but with an unsealed portion to provide said pouch with said one open end.

6. The package of claim 2 wherein said envelope comprises a pair of panels of sheet material sealingly connected together entirely around said envelope to seal the interior thereof.

7. The package of claim 6 wherein said pouch and envelope panels include plastic sheet material and are heat-sealed together.

8. The package of claim 5 wherein said envelope panels are bacteria-impervious.

9. The package of claim 8 wherein said envelope panels are of a thermoplastic sheet material.

10. The package of claim 9 wherein said pouch panels are of thermoplastic material.

11. The package of claim 10 wherein said pouch and envelope panels are pervious to a sterilizing gas.

12. A sterile package comprising an inner sterile flexible pouch openable at at least one end, a sterile article disposed wholly within said pouch, and an outer flexible envelope enclosing said pouch, said pouch having a portion thereof immovably restrained relative to said envelope before and after said envelope is opened, said envelope having a pair of facing panels and a weakened area on at least one side of said envelope for tearing said panels transversely between opposite sides of said envelope to divide it into a pair of envelope portions, each having an open end when manually pulled apart to open said envelope, said pouch extending within one of said envelope portions and terminating longitudinally between said weakened area and said one end of said envelope within the other of said envelope portions before said envelope is opened so that when said envelope is opened said pouch extends from within said one envelope portion and across said open end thereof so that when said article is removed from within said pouch and out said open end of said one envelope portion it will not contact said one envelope portion.

13. The package of claim 12 wherein said pouch includes a pair of inner panels of thermoplastic sheet material in facing relation, said envelope includes a pair of panels of thermoplastic sheet material in facing relation disposed on opposite sides of said pouch panels and enclosing the same, said pouch panels being heat-welded along marginal surfaces to each other and said envelope panels with ends of pouch panels at said one end of said pouch movable away from each other to permit egress of said article therefrom.

14. The package of claim 13, wherein each of said pouch panels has an edge which is angled inwardly toward the longitudinal axis of the envelope to provide relatively narrow flaps which extend across said open end of said one envelope portion.

15. The package of claim 12 wherein the longitudinal length of said panels is greater than that of said one envelope portion.

16. A sterile package comprising a pair of facing sterile panels, a sterile article disposed wholly between said panels, and an outer flexible envelope enclosing said panels and said article, said envelope having a pair of tear-lines of weakness extending transversely on opposite sides thereof dividing said envelope into a pair of envelope portions separable at said tear-lines so that each of said envelope portions has an open end when said envelope portions are manually pulled apart to open said envelope, said tear-lines being located longitudinally between said article and one end of said envelope, said panels being disposed within said envelope such that when said envelope is opened said panels extend from within one of said envelope portions and across said open end thereof so that when said article is removed from the opened package said article will move outwardly from between said panels and out the open end of said one envelope portion without contacting said one envelope portion, a portion of each of said panels being fixedly connected to said one envelope portion before and after said envelope is opened.

17. The package of claim 1 wherein said panels are separable at the end thereof which extends past said opening edge to permit egress of the article therefrom.

* * * * *